United States Patent [19]

Bryan et al.

[11] Patent Number: 5,226,225
[45] Date of Patent: Jul. 13, 1993

[54] METHOD OF MAKING A BIOMEDICAL ELECTRODE

[75] Inventors: Kathleen M. Bryan; Steven S. Kantner, both of St. Paul; Joseph L. Galatowitsch, Arden Hills; Terry G. Hargroder, Stillwater, all of Minn.; Jerome E. Strand, Hudson, Wis.

[73] Assignee: Minnesota Mining and Manufacturing Company, St. Paul, Minn.

[21] Appl. No.: 915,062

[22] Filed: Jul. 16, 1992

Related U.S. Application Data

[62] Division of Ser. No. 686,138, Apr. 16, 1991, Pat. No. 5,133,356.

[51] Int. Cl.[5] .............................................. H01R 43/00
[52] U.S. Cl. ........................................ 29/825; 29/878
[58] Field of Search ................... 29/825, 878; 128/640

[56] References Cited

U.S. PATENT DOCUMENTS

| | | | |
|---|---|---|---|
| 1,662,446 | 3/1928 | Wappler. | |
| 4,166,465 | 9/1979 | Esty et al. | 128/303 |
| 4,317,278 | 3/1982 | Carmon et al. | 29/878 |
| 4,409,981 | 10/1983 | Lundberg | 29/825 |
| 4,433,481 | 2/1984 | Szpur | 29/878 |
| 4,461,075 | 7/1984 | Bailey | 29/825 |
| 4,522,211 | 6/1985 | Bare et al. | 128/640 |
| 4,524,775 | 6/1985 | Rasmussen | 29/878 X |
| 4,539,996 | 9/1985 | Engel | 128/640 |
| 4,543,958 | 10/1985 | Cartmell | 128/640 |
| 4,580,339 | 4/1986 | Ioffe | 29/825 |
| 4,657,023 | 4/1987 | Kuhn | 128/640 |
| 4,679,563 | 7/1987 | Wada et al. | 128/640 |
| 4,694,835 | 9/1987 | Strand | 128/639 |
| 4,798,642 | 1/1989 | Craighead et al. | 156/252 |
| 4,827,939 | 5/1989 | Cartmell et al. | 128/640 |
| 4,852,571 | 8/1989 | Gadsby et al. | 128/639 |
| 4,856,188 | 8/1989 | Sibolis | 29/825 X |
| 4,922,911 | 5/1990 | Wada et al. | 128/640 |
| 4,945,911 | 8/1990 | Cohen et al. | 128/640 |
| 5,012,810 | 5/1991 | Strand et al. | 128/640 |

FOREIGN PATENT DOCUMENTS

0360496 9/1989 European Pat. Off. .
1519782 1/1975 United Kingdom .

OTHER PUBLICATIONS

Medical Instrumentation, Webster, pp. 245–247, (1978).
1205 Adult Monitoring Electrode depicted in "Our New Electrode System is a Snap?", Sentry Medical Products, (1989).

Primary Examiner—Carl J. Arbes
Attorney, Agent, or Firm—Gary L. Griswold; Walter N. Kirn; John H. Hornickel

[57] ABSTRACT

A biomedical electrode which generally comprises a conductor member partially overlapping a separator construction. The conductor member is preferably a thin flat, flexible member having a pad portion and a tab portion. The tab portion overlaps the separator construction in a manner which centrally positions mechanical and electrical contact of electrode with an electrical lead to electrical instrumentation. Beneath pad portion and all or a substantial portion of separator construction is a conductive adhesive to provide good electrical interface between skin of a subject and the electrical instrumentation. Methods of manufacturing biomedical electrodes from strips of components are also disclosed.

3 Claims, 3 Drawing Sheets

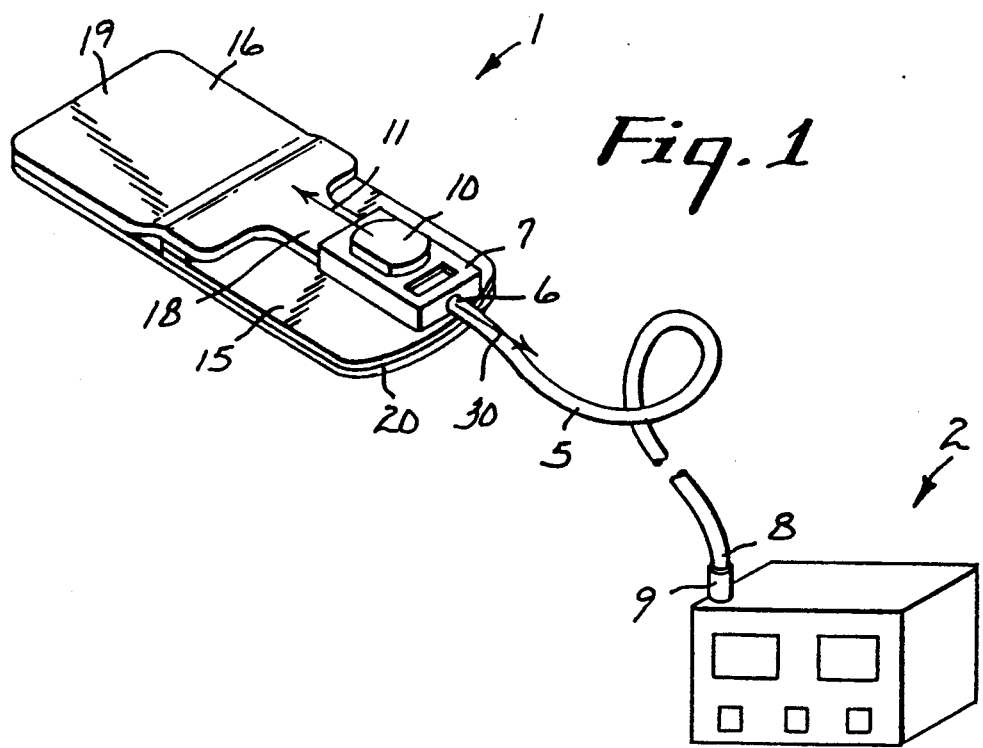
Fig. 1
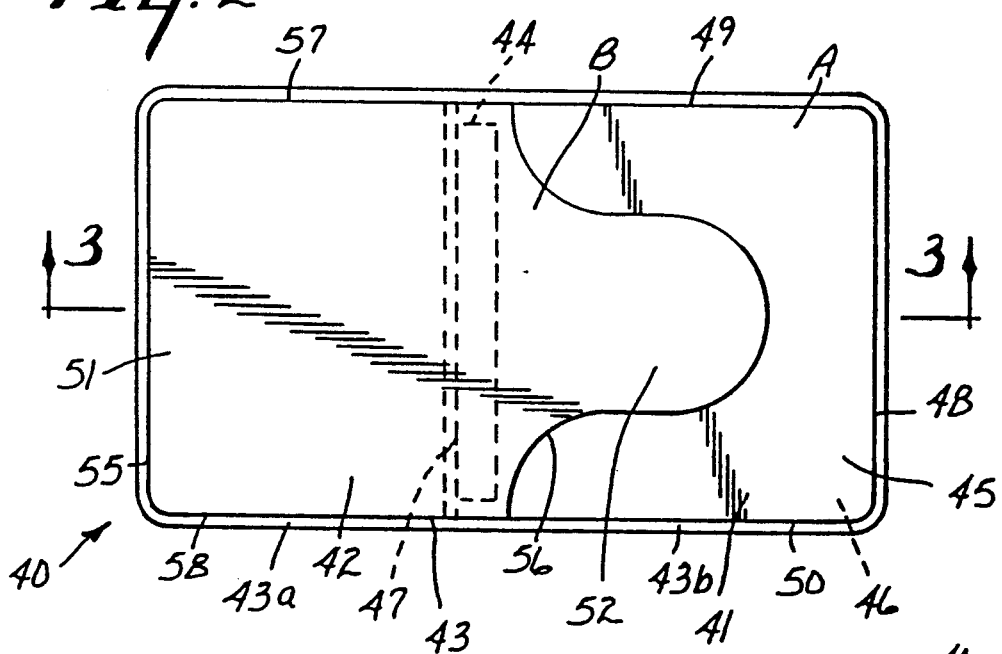
Fig. 2
Fig. 3

METHOD OF MAKING A BIOMEDICAL ELECTRODE

This is a division of application Ser. No. 07/686,138 filed Apr. 16, 1991, now U.S. Pat. No. 5,133,356 issued Jul. 8, 1992.

FIELD OF THE INVENTION

The present invention relates to flexible, low-profile, skin-adhering biomedical electrodes which have an electrically conductive contacting tab centrally-positioned on an outer surface and within a perimeter of the biomedical electrode.

BACKGROUND OF THE INVENTION

Electrocardiography is the well-established, but still rapidly developing, science of making and studying graphic records (electrocardiograms) generated by electrical currents originating in an animal heart, most often a mammalian heart.

An electrocardiogram (ECG) is measured through utilization of an electrocardiograph instrument, which monitors the electric potentials associated with those electric currents that transverse the heart.

In practice, electrodes are positioned on the skin surface of the subject to be evaluated. Those electrodes are in electrical communication with the electrocardiograph instrumentation. The electrodes must generally be such as can accurately detect and transmit electrical signals produced by various biological events.

An acceptable biomedical electrode has an adequate conductive surface for receipt of electrical signals from the body, a good conductive interface between the electrical instrumentation and the subject, and sufficient adherence of the electrode during the period of evaluation.

Electrocardiography has been applied in a variety of circumstances including: in resting diagnostic procedures; in surgical and emergency room procedures; in cardiac units; in critical care units; in ambulatory monitoring; in stress diagnostic procedures; and in more continual, or intermittent, monitoring as selected for a person not under constant supervision and not substantially restrained with respect to activity.

Thus, the period of evaluation and the condition of evaluation environment can differ among the various types of ECG procedures Regardless of the period of evaluation or condition of evaluation environment, an acceptable biomedical electrode must perform adequately to be a useful evaluation component: adequate conductive surface, good conductive interface, and continued skin adherence during the period of evaluation.

Another factor in the acceptability of a biomedical electrode is cost. Due to hygiene and other expense of re-use considerations, many biomedical electrodes are designed to be disposable after a single use. Biomedical electrodes used during limited periods of evaluation, such as resting, emergency, or surgical diagnosis, can be constructed and priced for a single use before disposal.

Biomedical electrodes have been known to provide an electrically conductive tab extending beyond the perimeter of the conductive surface area of the biomedical electrode. Examples of biomedical electrodes of this type are disclosed in U.S. Pat. No. 4,539,996 (Engel), U.S. Pat. No. 4,543,958 (Cartmell), U.S. Pat. No. 4,694,835 (Strand), and U.S. Pat. No. 4,852,571 (Gadsby et al.). An electrically conductive tab extending beyond the perimeter of the conductive surface area of the biomedical electrode requires mechanical and electrical contact in an area adjacent to skin of a subject.

Other biomedical electrodes provide an electrically conductive tab within the perimeter of the conductive surface area of the biomedical electrode by having the tab emerge from a skin contacting side of the electrode through a slit or seam in the outer protective layer of the electrode. Examples of biomedical electrodes of this type are disclosed in U.S. Pat. No. 1,622,446 (Wappler), U.S. Pat. No. 4,166,465 (Esty), U.S. Pat. No. 4,852,571 (Gadsby et al.), European Patent Publication 0 360 496 (Strand et al.), and British Patent Specification 1 519 782 (Osborn et al.). Production of electrodes of this type require elaborate manufacturing techniques to make a slit or form a seam, with the tab extending therethrough.

Still other biomedical electrodes provide an electrically conductive tab within the perimeter of the conductive surface area of the biomedical electrode by having the outermost protective layer cut along a line within the perimeter of protective layer to form a tab from the protective layer. Examples of biomedical electrodes of this type are disclosed in U.S. Pat. No. 4,657,023 (Kuhn), U.S. Pat. No. 4,679,563 (Wada et al.), and U.S Pat. No. 4,922,911 (Wada et al.). Production of electrodes of this type also require elaborate manufacturing techniques to make a cut in the outermost protective layer and creating an electrically conductive tab therefrom which can be lifted from the remainder of the protective layer for use.

SUMMARY OF THE INVENTION

The present invention provides an inexpensively-made biomedical electrode which has a good conductive surface area, good conductive interface between the subject of evaluation and the electrical instrumentation, and sufficient adherence of the electrode to the skin of the subject for the period of evaluation and the conditions of the evaluation environment.

The biomedical electrode of the present invention comprises (a) a separator construction comprising a flat sheet having a first and second opposite sides and edges between the sides defining a perimeter; and (b) a conductor member having a pad portion and a tab portion, the conductor member being oriented in the electrode with the pad portion having a side coplanar with the second side of the separator construction, and with the tab portion in a plane above and overlapping the first side of the separator construction; the tab portion having an area smaller than an area of the first side of the separator construction whereby mechanical and electrical connection of the biomedical electrode is centrally-positioned within the perimeter.

In this description, "centrally-positioned" means that the conductor member is secured or otherwise aligned to the separator construction at a position on the first side of the separator construction such that the tab portion of the conductor member does not extend beyond a perimeter of the biomedical electrode.

The biomedical electrode of the present invention further comprises a field of conductive adhesive contacting the side of the pad portion and optionally also the second side of the separator construction. The biomedical electrode further comprises means of adhering the conductor member to the first side of the separator construction, whereby the conductor member tab portion is adjacent to, but not adhered directly to, the separator construction.

Biomedical electrodes according to the present invention include a substantially flat, flexible, conductor member having a pad portion and a tab portion. The pad portion is arranged and oriented to receive electrical signals from the subject's body. The tab portion, on the other hand, is available for engagement with a wire lead or the like, to provide electrical communication to electrical instrumentation such as an electrocardiograph monitor.

Substantially flat conductor members according to the present invention can be formed from a relatively thin layer of flexible polymeric material, such as a polyester film, having a conductive layer, such as a silver/silver chloride material, a metal foil or laminate, (e.g., a vinyl-laminated tin foil), or a non-woven web impregnated with conductive carbon ink, on at least one side thereof. Preferred such materials, being relatively thin, are very flexible, and can be readily and easily mounted in the arrangements required by the invention. Further, depending on the nature and amount of metal employed, they can be relatively transparent to X-ray, so a person wearing biomedical electrodes according to preferred embodiments of the present invention can be examined by X-ray without significant problems from strong shadows. That is, the person need not be bothered by removal and remounting of the biomedical electrodes, in order for routine X-ray examinations or the like to occur.

Conductive adhesive capable of biocompatibly adhering to skin can be generally either a conductive adhering or "sticky" gel or a conductive pressure-sensitive adhesive. A variety of conductive adhesives known to those skilled in the art can be utilized to provide both good electrical interface between the subject and the electrical instrumentation and good adhesion during the period of evaluation of the subject. Non-limiting examples of conductive adhesives include conductive adhesives disclosed in U.S. Pat. Nos. 4,539,996; 4,554,924; and 4,848,353 (all Engel and incorporated by reference herein) and U.S. Re. Pat. Nos. 31,454 (Hymes) and 4,391,278 (Cahalan).

A separator construction segregates the conductive material from the tab portion of the conductor member and also protects the conductive adhesive from contact with the environment during the period of evaluation. The separator construction can be made of a number of electrically insulative materials, preferably polymeric film materials, and more preferably, transparent or translucently polymeric film materials. Transparency or translucency through the separator construction permits visual inspection of the condition of the conductive adhesive and its interface with and condition of skin beneath. Non-limiting examples of polymeric film materials include polyolefins (e.g., polyethylene and polypropylene), polyesters, and polyurethanes.

Alternatively, the separator construction can have an electrically conductive surface on the side contacting conductive adhesive. The electrically conductive surface can be useful to increase surface area of electrical interface between conductive adhesive and the pad portion of the conductor member. Certain diagnostic and monitoring circumstances can require such larger surface area. Alternatively, the biomedical electrode of the present invention can distribute electrical energy to skin of a subject, as in electrotherapy. In that instance, having an electrically conductive surface area on separator construction can evenly distribute such electrical energy to all areas of the conductive adhesive.

Optionally, a means to adhere the conductor member to the separator construction can be employed to centrally-position the conductor member on the biomedical electrode. Non-limiting examples of the means of adhering can include a separate field of pressure-sensitive or hot melt adhesive, a double-stick pressure-sensitive adhesive tape, or a portion of the separator construction having an adhesive surface contacting the conductive adhesive being folded back to provide an adhesive surface to contact the conductor member.

The field of conductive adhesive can contact substantially the entire area of both pad portion of conductor member and the entire area of separator construction accessible for contact. Alternatively, the field of conductive adhesive can contact substantially the entire area of pad portion of conductor member and a biocompatible skin adhesive can contact substantially the entire area of separator construction.

Preferably, a portion of separator construction can extend beyond the field of conductive adhesive or skin adhesive contacting the remainder of separator construction, to create a non-adhering lift tab to facilitate placement and removal of the electrode prior to and at the conclusion of the period of evaluation.

In general, when first manufactured the biomedical electrode will include a protective release liner or the like secured to the first side of the insulator construction. The release liner can be selectively separated from the conductive adhesive to expose its outer surface for application to a subject. A variety of materials may be utilized as a release liner, for example a silicone-coated polypropylene or polyester material might be utilized.

The release liner can be coterminous with the dimensions of the adhesive areas of the biomedical electrode or can extend beyond the dimensions thereof.

In other embodiments, a spacer or tab positioned between a portion of the release liner and the conductive adhesive can be used to facilitate separation.

Also, an array of biomedical electrodes can be arranged on a single release liner, with the number of electrodes on the liner being chosen for convenience of the health care practitioner.

It is a feature of the present invention that the centrally-positioned tab portion facilitates ease of good, secure, conductive connection to an electrocardiograph lead.

It is another feature of the present invention that the biomedical electrode is constructed of flexible, conformable materials to maximize adherence of the biomedical electrode to skin of a subject regardless of the contours of skin where adhesion must occur.

It is another feature of the present invention that the biomedical electrode is constructed of relatively thin materials to provide a low-profile which minimizes obstruction or disruption with other equipment, clothing, manual medical procedures or the like.

It is another feature of the present invention that the biomedical electrode is constructed of materials less likely to cause an image on X-ray photographs of the area of the subject near the location of electrode placement.

It is another feature of the present invention that the centrally-positioned tab portion provides good, secure, conductive connection to an electrocardiograph lead within the perimeter of the biomedical electrode.

It is another feature of the present invention that the centrally-positioned tab portion facilitates connection to electrical instrumentation without application of significant deleterious stress to the adhesive interface between the electrode and the subject. In general, this avoidance of stress to the biomedical electrode minimizes adhesive failure at the skin surface.

It is another feature of the present invention that the biomedical electrode provides a good conductive interface between the electrode and the subject's body. In general, this is provided by use of a conductive adhesive positioned between a conductive portion of the electrode and the subject's body.

It is another feature of the present invention that the biomedical electrode is configured and made of materials to maximize flexibility during use. For example, due to its flexible construction, the biomedical electrode of the present invention can be easily positioned in engagement with a portion of a subject's body. Should the subject move or twist while the biomedical electrode of the present invention is in position, the electrode can readily flex or bend to accommodate the movement and/or twists of the subject's body.

It is an advantage of the present invention that ends of the leads attachable to the electrodes possibly having electrically conductive portions at least partially exposed thereat are unlikely to come into direct contact with a subject's body; come into direct contact with electrolyte gel and/or conductive adhesive; and/or come into contact with adjacent leads and/or electrodes. As a result, better electrical signals can be recorded without interfering signals. Also as a result, leads or other clips are less likely to become contaminated or dirty with body exudate, conductive adhesive and the like.

It is another advantage of the present invention that biomedical electrodes can be made relatively inexpensively and efficiently constructed.

Methods of construction of the biomedical electrode can provide a mass production of an array of electrodes on a single release liner without the need for establishing the position of the tab portion through a slit or seam or formed from a portion of the outermost layer of the electrode.

Sequential layering of components of biomedical electrodes can facilitate mass production of an array of electrodes, which are then separated by cutting into individual electrodes while on the release liner.

A method of making biomedical electrodes comprises (a) positioning on a release liner a strip of conductive adhesive having opposing first and second edges along the strip; (b) overlaying a strip of separator construction, having opposing first and second edges along the separator construction strip, on the conductive adhesive in a position of the first edge of the separator construction relative to the first edge of the conductive adhesive strip; (c) overlaying a means for adhering on the separator construction in a position relative to the second edge of the separator construction; (d) overlaying a strip of conductor members, each having a tab portion, a pad portion, and pad portion edge, on the conductive adhesive and the means for adhering in a position of each pad portion edge aligned with the second edge of the conductive adhesive to form an electrode subassembly, whereby the tab portion is in a plane above and overlapping the strip of separator construction; and (e) separating the electrode subassembly between adjacent tab portions of the conductor members.

Another method of making biomedical electrodes of the present invention comprises (a) providing a strip of conductor members, each member having two tab portions at opposing edges of the strip and two pad portions integral and continuous on the strip; (b) overlaying a means for adhering on the strip of conductor members on each tab portion in a position substantially adjacent to each pad portion; (c) overlaying a separator construction on each means for adhering and over each tab portion of each conductor member; (d) overlaying a field of conductive adhesive over each pad portion of each conductor member and optionally over each separator construction to form an electrode array; (e) overlaying a release liner on the electrode array; (f) cutting the electrode array on the release liner along a line between adjacent tab portions; and (g) cutting the electrode array along a line between continuous pad portions, whereby a plurality of individual biomedical electrodes, each having a centrally positioned tab portion, are provided on the release liner.

It is another feature of the present invention that relatively inexpensive components and mass manufacturing techniques can be utilized.

It is an advantage of the present invention that an inexpensively-made, flexible, low-profile, biomedical electrode can provide a good conductive surface area, good conductive interface, and adherence to skin for the period of evaluation.

The use of the biomedical electrode of the present invention can demonstrate its advantages over other biomedical electrodes previously known and used.

A lead from electrocardiograph or other electrical instrumentation is attached to the tab portion.

Biomedical electrodes of the present invention can be used with a number of types of biomedical instrumentation. Biomedical electrodes of the present invention can be used with electrocardiographs or other electrical receiving instrumentation for diagnostic, monitoring, stress, or other testing detecting a subject's electrical signals. Biomedical electrodes of the present invention also can be used with therapeutic electrical instrumentation such as transcutaneous electronic nerve stimulation (TENS) devices used for pain management and neuromuscular stimulation (NMS) used for treating conditions such as scoliosis. Biomedical electrodes of the present invention also can be used as dispersive electrodes or "grounding plates" for electrosurgery or as defibrillation pads for cardiac emergency treatment. Typically, the electrical connection is provided by means of a clip or clasp element which can be attached to the conductor member tab portion. Due to the location of the tab portion positioned centrally on the outer surface of the electrode, the clip or clasp, having electrically conductive elements therein, is insulated from direct contact with the subject's body. That is, it is unlikely that the clip or clasp will receive electrical signals other than through the conductive member. As a result, the arrangement of the present invention provides for relatively low likelihood of unintended noise interrupting the desired signal to be received by the electrical instrumentation. Further, it is most unlikely that a clip will contact or pinch skin of a subject of evaluation or that a reusable clip will become contaminated by body oils or adhesive. Further, it is unlikely that twisting of clip or clasp during inadvertent movement of the subject relative to the electrical instrumentation will cause a loss of adhesion of the electrode at the skin of the subject.

It will be seen from the embodiments of the invention and drawings described below that an insulation of the clip or clasp from the subject's body is achieved in a secure manner without the need for adhesive tape or the like being used to maintain or retain the clip in position. This facilitates attachment and detachment of the clip as necessary, and further facilitates subject comfort.

The drawings constitute a part of this specification and represent preferred embodiments of the invention. It will be understood that, in some instances, relative component sizes and/or material thicknesses may be shown exaggerated, to facilitate an understanding of the invention.

BRIEF DESCRIPTION OF THE DRAWING

FIG. 1 is a perspective view of a biomedical electrode according to the present invention, shown in an environment of association with an electrocardiograph monitor and with a lead extending from the electrode to the monitor.

FIG. 2 is a top plan view of a biomedical electrode according to the embodiment of FIG. 1; dotted lines indicating selected portions hidden from view.

FIG. 3 is an enlarged side cross sectional view taken generally along line 3—3, of FIG. 2, except that the device of FIG. 3 does include a release liner.

Embodiments of the Invention

Figure 4:
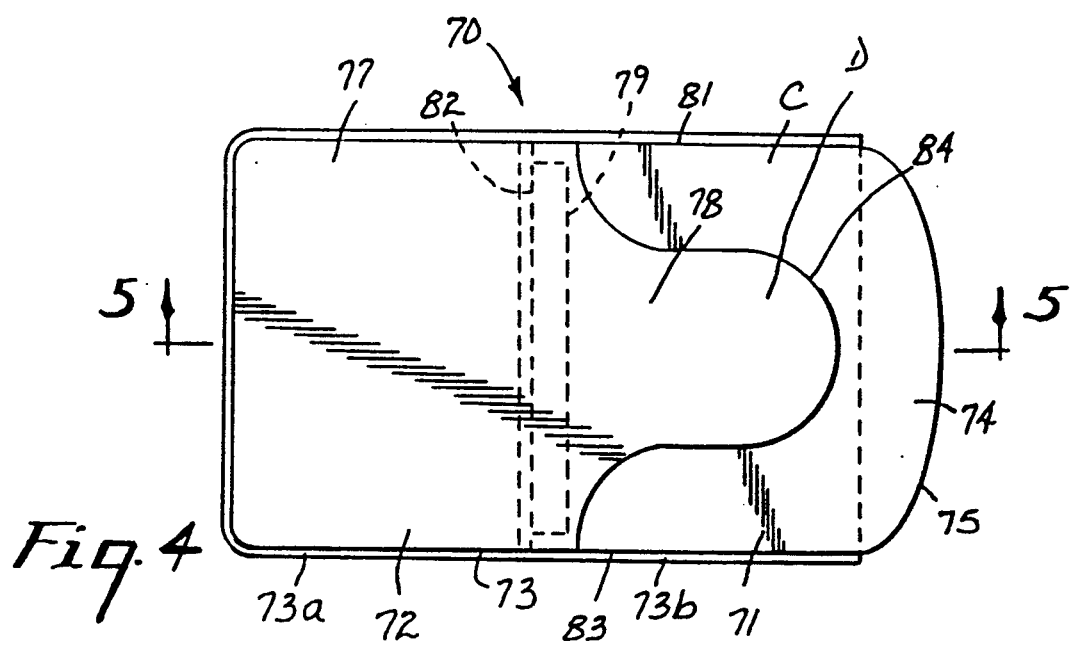
FIG. 4 is a top plan view of a second embodiment of a biomedical electrode; dotted lines indicating selected portions hidden from view.

Detailed descriptions of certain embodiments of the present invention are provided hereinbelow. It is to be understood that the embodiments described and shown are representative only, and that the present invention may be embodied in various forms not depicted or specifically described in detail.

The reference numeral 1, in FIG. 1, generally designates a biomedical electrode according to the present invention. The electrode 1 is depicted in perspective, and is shown in association with electrical diagnostic instrumentation 2, such as an electrocardiograph monitor. Monitor 2 can be portable, mobile, or stationary.

Electrical communication between electrode 1 and instrumentation 2 is generally provided by means of a lead 5 having a first end 6 attached to a clip or clasp 7, and a second end 8 attached to a jack 9 or the like, for engagement with instrumentation 2. A variety of clips 7 may be utilized. The one shown in FIG. 1, includes a thumb operated cam 10 which, when slid in the direction indicated by arrow 11, causes gripping of a thin, flat member, in particular a tab portion of electrode 1 described below. Clip 7 is described in U.S. Pat. No. 4,700,997 (Strand), which is incorporated by reference herein. Other clips useful including "alligator" clips commonly used in the art and a clip described in U.S. Pat. No. 4,842,558 (Strand) which is incorporated by reference herein. Alternatively, the mechanical and electrical contact at tab portion can be pre-wired to a lead wire 5, which is useful in certain circumstances where attachment of a clip to an electrode is difficult, such as with premature infants.

Electrodes 1 according to the present invention include two primary non-adhesive components: a flexible separator construction 15 and a substantially flat, flexible, conductor member 16. A preferred association between conductor member 16 and separator construction 15 yields many of the advantages of the present invention.

Still referring to FIG. 1, conductor member 16 generally includes a tab portion 18 and a pad portion 19. According to the present invention, the conductor member 16 is oriented relative to the separator construction 15 such that the pad portion 19 is substantially coplanar with the separator construction 15 and the tab portion 18 is generally above the plane of the insulator construction 15 and the pad portion 19.

It is noted that tab portion 18 of conductor member 16 includes that portion of the conductor member 16 engagable by clip 7. Typically, for preferred embodiments, the tab portion 18 will be a rather elongate, narrow, extension of conductor member 16. Other shapes are contemplated as also useful, provided that the tab portion remains centrally-positioned. A non-limiting example includes a shape of tab portion 18 that has a larger surface area for mechanical and electrical contact but which remains within the perimeter of the biomedical electrode 1.

The pad portion 19 of conductor member 16 is that portion of the conductor member 16 which receives electrical signals from the subject's body. In general, it is preferred that the pad portion 19 be relatively large in gross surface area. The term "gross surface area" used herein means the surface area resulting from the overall outside perimeter dimensions of pad portion 19, and not necessarily to that surface area which can be measured by microscopic examination of the conductor surface of pad portion 19. The term "surface area" or "gross surface area" as used herein in this context is meant to refer to one side only of the pad portion 19. For typical, preferred embodiments of the present invention, to be used as adult human bioelectrodes, the pad portion 19 should have an overall surface area of about 0.65 to 6.5 $cm^2$. Also, the tab portion 18 should have an overall length of about 1.0-3.0 cm and a width of about 0.6-2 cm. It is noted that the pad portions shown in the drawings are roughly 60% wider than they are long, however a variety of sizes and shapes may be used.

FIG. 1 also shows that a field 20 of conductive adhesive is applied to conductor member pad portion 19 and optionally to separator construction 15 on the surfaces opposite from exposure to clip 7. The conductive adhesive 20 is generally either an adhering or "sticky" electrolyte gel, or a conductive pressure-sensitive adhesive. For preferred embodiments of the present invention, conductive pressure-sensitive adhesive is used, as it provides not only for good conductive association between the pad portion 19 and the user's body, but it also facilitates adhesion, i.e., maintenance over time of a good association. A variety of conductive adhesives may be utilized, and all that is generally required is that the material function to provide for good electrical contact between pad portion 19 and the subject's body.

Preferred conductive adhesives are described in greater detail below.

The size and configuration of tab portion 18 shown in FIG. 1 illustrates the advantages of a biomedical electrode 1 of the present invention. The tab portion 18 entirely resides within the perimeter of electrode 1, comprising the edges of conductor member pad portion 19 and separator construction 15. The tab portion also resides in the plane above separator construction but is sized and shaped to reside within its perimeter.

Thus, the tab portion 18, and any clip 7 in association therewith, is completely insulated or separated from the user's body by the separator construction 15. In this manner, direct contact between clip 7 (and any conductive elements thereon), and the user's body is unlikely. This will inhibit the generation of undesired noise or signals in the system for electrocardiograph monitoring. Further, direct contact between a clip 7 and the user's body is minimized for other electrical instrumentation.

The substantially flat construction depicted in FIG. 1 leads to significant advantages. For example, it is foreseen that as the user attaches or detaches clip 7, or goes about ordinary movement with electrode 1 and clip 7 in position, significant tugging or pulling on tab portion 18 may occur. For the most part, due to the flat construction of electrode 1, the major component of this force will typically be directed in the general direction indicated by arrow 30. That is, it will generally be directed parallel to a plane of flat electrode 1 and parallel to the body of a user to which electrode 1 may be attached. This type of force is a shearing force operating on the field 20 of conductive adhesive between separator construction 15 and the user's body. Since there is relatively little component causing much separation between the two, but rather most of the tugging component will be shear, separation will be less likely to occur. This can be a significant advantage to the present invention, over arrangements wherein a less flat construction is utilized. Alternately phrased, the construction of the electrode 1 is such that typical forces due to tugging on the lead wire 5 are not likely to "lift" the electrode 1 from the subject.

The centrally-positioned tab portion 18 also resists the effects of twisting of the mechanical contact between the lead wire 5 and electrode 1. By securement of the conductor member 16 to the separator construction 15 in a location that centrally positions the tab portion 18, typical forces due to twisting on the lead wire 5 are less likely to twist and lift any edge of the electrode.

Another advantage of the rather flat construction is that the electrode 1 will be less conspicuous when worn under the user's clothes and less obstructive to other medical procedures. Further, the arrangement can be readily manufactured, manipulated and applied.

It will also be understood that the rather flat, flexible construction does not provide for any substantial projections that might be likely to cause discomfort for a user, should the user be bumped in the vicinity of the worn electrode or should the subject lie down.

A further view of an embodiment of the invention is depicted in FIGS. 2 and 3. Referring to FIG. 2, the electrode 40 depicted therein is generally the same as electrode 1 in FIG. 1. Electrode 40 includes an insulating separator construction 41, a conductor member 42, a field 43 of adhesive contacting areas of both separator construction 41 and conductor member 42, and an adhesive means 44 between separator construction 41 and conductor member 42.

As seen in FIG. 3, field 43 of adhesive can be separated into two portions: portion 43a which contacts conductor member 42 and portion 43b which contacts separator construction 41. Whereas field portion 43a is a conductive adhesive, field portion 43b can be a biocompatible adhesive, such as a conductive adhesive or a biocompatible skin adhesive which is not necessarily conductive. Depending on the surface area of electrical interface desired, the relative sizes of field portions 43a and 43b can also vary, so long as an adequate area of field portion 43a contacts conductor member 42 to provide useful electrical interface.

For the embodiment of FIG. 2, the separator construction 41 has opposite sides 45 and 46, with side 45 being an exposed surface near connection of conductor member 42 with clip 7 and surface 46 being in contact with field 43 of conductive adhesive in both portions 43a and 43b. Between opposite sides 45 and 46 are opposing edges 47 and 48, with edge 47 proximal to conductor member 42 and edge 48 distal to conductor member 42. Separator construction 41 has opposing edges 49 and 50 between edges 47 and 48 to define an area "A" on side 45. Separator construction side 45 has a larger surface area "A" than the surface area "B" of any portion of conductor member 42 in a plane above side 45. The combinations of edges 47, 48, 49, and 50 define a perimeter of the surface area "A" within which conductor surface area "B" is contained.

Conductor member 42 has a pad portion 51 generally corresponding to pad portion 19 in FIG. 1 and a tab portion 52 generally corresponding to tab portion 18 in FIG. 1. Pad portion 51 has an exposed side 53 and a conductive interface side 54 opposed thereto (as seen in FIG. 3). Between sides 53 and 54 are an edge 55 distal to the separator construction 41 and a curving edge 56 which defines the shape of tab portion 52 in the plane above area A of the separator construction 41. Shape of tab portion 52 is defined by the shape of curving edge 56, which can vary in any manner which result in an area "B" within area "A". Between edges 55 and 56 are opposing edges 57 and 58 which define a width of pad portion 51 approximately the same width as the width of separator portion 41 between edges 49 and 50.

Tab portion 52 defined by curving edge 56 overlaps side 45 of separator construction 41. As seen in FIG. 3, tab portion 52 is above a plane defined by the relative coplanar positions of separator construction 41 and pad portion 51. As seen in FIG. 2, area B comprising the portion of overlap of tab portion 52 over separator construction 41 is centrally-positioned within the edges 48, 49, and 50 of side 45 of separator construction 41.

To secure the relative position of tab portion 52 above the side 45 of separator construction 41, a means for adhering, e.g., a strip 44 of adhesive is placed at the point of overlap of tab portion 52 over edge 47 of separator construction 41. As seen in FIG. 2, this strip 44 extends substantially between edges 57 and 58 of conductor member 42 and substantially adjacent to the points of intersection of curved edge 56 with edges 57 and 58.

Strip 44 also raises slightly tab portion 52 from contact with side 45 of separator construction 41, such that tab portion 52 is adjacent to, but not directly adhered to, separator construction 41 at side 45. This slight elevation of tab portion 52 above side 45 also facilitates the mechanical and electrical connecting of tab portion 52 with clip 7 as seen in FIG. 1.

Contacting side 54 of pad portion 51 of conductor member 42 is a field portion 43a of conductive adhesive. In this embodiment, conductive adhesive is also used as field portion 43b to contact side 46 of separator construction 41, although conductive adhesive can be replaced by a skin adhesive. As seen in FIG. 2, field 43 substantially extends from edge 57 to edge 58 beneath pad portion 51 and from edge 49 to edge 50 beneath separator construction 41. Also, field 43 substantially extends from edge 48 of separator construction 41 to edge 55 of pad portion 51. Side 54 of pad portion 51 provides good electrical and adhering contact between pad portion 51 and field portion 43a. Side 46 of separator construction 41 provides protection of field portion 43b from exposure to the environment.

Thus, the positioning and securement of conductor member 42 on side 54 causes the establishment of a good electrical interface between field portion 43a and conductor member 42, and the establishment of a field portion 43a, and optionally field portion 43b, of conductive adhesive of adequate size and sufficient adhering properties to maintain good electrical interface between the electrical instrumentation and the skin of the subject for the period of evaluation.

In FIG. 3, a layer of release liner 60 is shown positioned against that side of electrode 40 which has field 43 of adhesive(s) thereon. Preferably, the release liner 60 will directly contact only field 43 and not other components of electrode 40.

In general, after manufacture and during storage, electrode 40 will be maintained with release liner 60 protecting the field 43 of adhesive(s). It is foreseen that the release liner 60 will generally be stripped from the arrangement 40 immediately prior to use. A variety of release liners 60 may be utilized; for example, a liner comprising a polymer such as a polypropylene or polyester material, coated with a silicone release type coating which is readily separable from the skin adhesive and conductive adhesive. In some embodiments, it may be desired to place a spacer or tab (not shown) between release liner 60 and a portion of field 43 of adhesive(s) to facilitate the separation.

It will be understood that the dimensions of the various layers, and their conformation during association, are shown somewhat exaggerated in FIG. 3, to facilitate an understanding of the invention. In general, an overall substantially flat appearance with only a very minor "s" type bend between pad portion 51 and tab portion 52 of conductor member 42 is accommodated by the arrangement.

Figure 5:
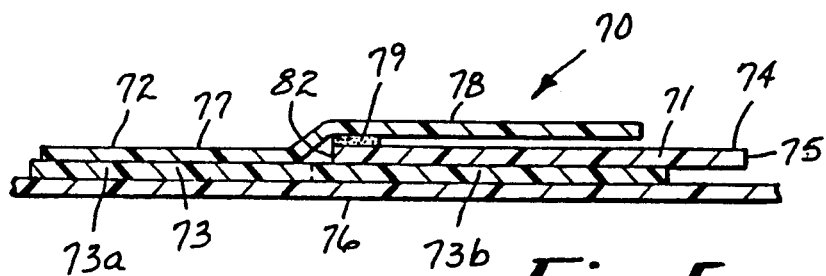
FIG. 5 is an enlarged side cross sectional view taken generally along line 5—5, of FIG. 4, except that the electrode of FIG. 5 does include a release liner.

FIGS. 4 and 5 illustrate an alternate embodiment of the biomedical electrode of the present invention.

Biomedical electrode 70 conforms in analogous respect to biomedical electrode 40 seen in FIGS. 2 and 3 with some exceptions. Separator construction 71 differs from separator construction 41. At a location distal from conductor member 72, separator construction 71 extends beyond field 73 of adhesive at portion 73b distal from field portion 73a. There, separator construction 71 provides a lift tab portion 74 for facile removal of electrode 70 from a release liner 76, placement of electrode on skin of a subject, and subsequent removal of electrode 70 from skin of a subject at the end of the evaluation period. The edge of the lift tab portion 74 can be curved as seen in FIG. 4 to minimize a corner snagging on clothing or equipment during use.

Referring to FIG. 5, the remaining portions of electrode 70 are analogous to electrode 40. Conductor member 72 has a pad portion 77 contacting field portion 73a of conductive adhesive and a tab portion 78. Conductor member 72 is adhered to separator construction 71 by a double stick adhesive strip 79 positioned at the area of overlap of tab portion 78 over separator construction 71.

Biomedical electrode 70 seen in FIGS. 4 and 5 also provides an area C defined by a perimeter of edges 75, 81, 82, and 83 of separator construction 71. Area C is larger than conductor surface area D defined by the shape of tab portion 78 curving edge 84. Thus, tab portion 78 is centrally positioned within the perimeter of the biomedical electrode.

Figure 6:
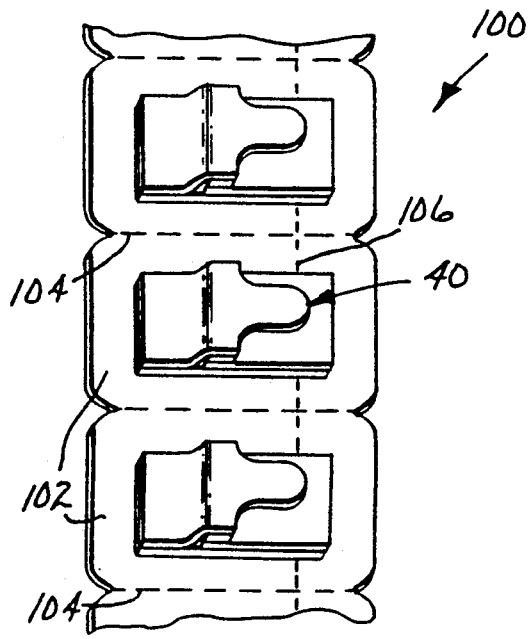
FIG. 6 is a top plan view of a one embodiment of an assembly of biomedical electrodes.

The structure of electrode 40 and electrode 70 simplifies manufacturing and avoids creation of slits, seams, or cuts to expose the centrally-positioned tab portion 52 or 78. For example, a strip or other plurality of electrodes can be arranged on a release liner during making the electrodes for facile distribution and application to a subject's skin FIG. 6 illustrates a strip 100 of electrodes, which can be either electrodes 40 or electrodes 70. In FIG. 6, the strip 100 of electrodes 40 are assembled onto a strip of release liners 102 which are interconnected at edges having perforated lines 104. The electrode strip 100 may be dispensed sequentially or packaged in a folded manner to minimize storage space. At the time of use, as seen in FIG. 6, a perforated line 106 in one liner 102 may be torn to peel electrode 40 from liner 102 to expose the field 43 of adhesive(s). It is desirable to place the perforated line 106 at a location along a line beneath field 43 to facilitate removal of electrode 40 from liner 102.

Figure 7:
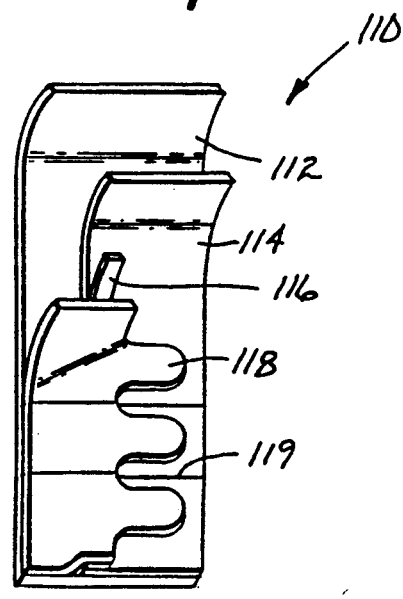
FIG. 7 is an illustrative view of first steps of a means of assembly of a biomedical electrode subassembly useful for providing a strip of biomedical electrodes.

The strip 100 of electrodes 40 or 70 illustrated in FIG. 6 can be assembled with a minimum number of steps, which economizes manufacturing processes. FIG. 7 illustrates a method of preparing electrode 40 or 70 useful to prepare strip 100.

FIG. 7 shows the construction of an electrode strip subassembly 110 which has a laminate construction comprising a strip of conductive adhesive 112, a strip of separator construction 114, a strip of double-stick adhesive 116, and strip 118 of a series of unseparated conductor members. Each strip is sequentially aligned as shown in FIG. 7 according to processes and with equipment known to those skilled in the art for assembly of laminate constructions including adhesive layers. U.S. Pat. No. 4,795,516 (Strand) and U.S. Pat. No. 4,798,642 (Craighead), which are incorporated by reference herein, disclose processes and equipment useful for dispensing strips of material from rolls and overlaying such strips in a registered, continuous manner in order to prepare a strip subassembly 110. The width of the electrode strip subassembly 110 is about 2-8 cm and preferably about 4 cm.

At lines 119, the strip subassembly 110 is cut, preferably with a standardized die, to provide a number of individual electrodes 40, having appropriate dimensions, presently preferred to be 1.8 cm wide and 4 cm long. Each electrode 40 comprises, in order of assembly from bottom to top and identified with reference to FIG. 2, a field 43 of adhesive(s), separator construction 41, double-stick adhesive strip 44, and conductor member 42, having a pad portion 53 contacting field portion 43a of conductive adhesive, and a tab portion 52 adhered to double-stick adhesive 44.

As seen again in FIG. 6, each electrode 40 can be applied to a strip 100 of release liners 102 by contacting each field 43 of adhesive(s) with each liner 102. Each electrode 40 is preferably positioned on each liner 102 above perforated line 106.

With means known to those skilled in the art to achieve an appropriate registration, one can place a series of electrodes 40 or electrodes 70 on a strip 100 of release liners 102 separated by perforated lines 104, such as that seen in FIG. 6, to minimize complications of biomedical electrode construction. U.S. Pat. Nos. 4,795,516 and 4,798,642 disclose processes and equipment useful for assuring such registration of electrodes between perforated lines 104 and over perforated lines 106.

This method of construction shown in FIG. 6 reduces expense of manufacture and permits sequential mass production of biomedical electrodes 40 or 70 into a strip of electrode subassembly 110 such as that seen in FIG. 6 die cut for placement on liners 102 of strip 100.

Figure 8:
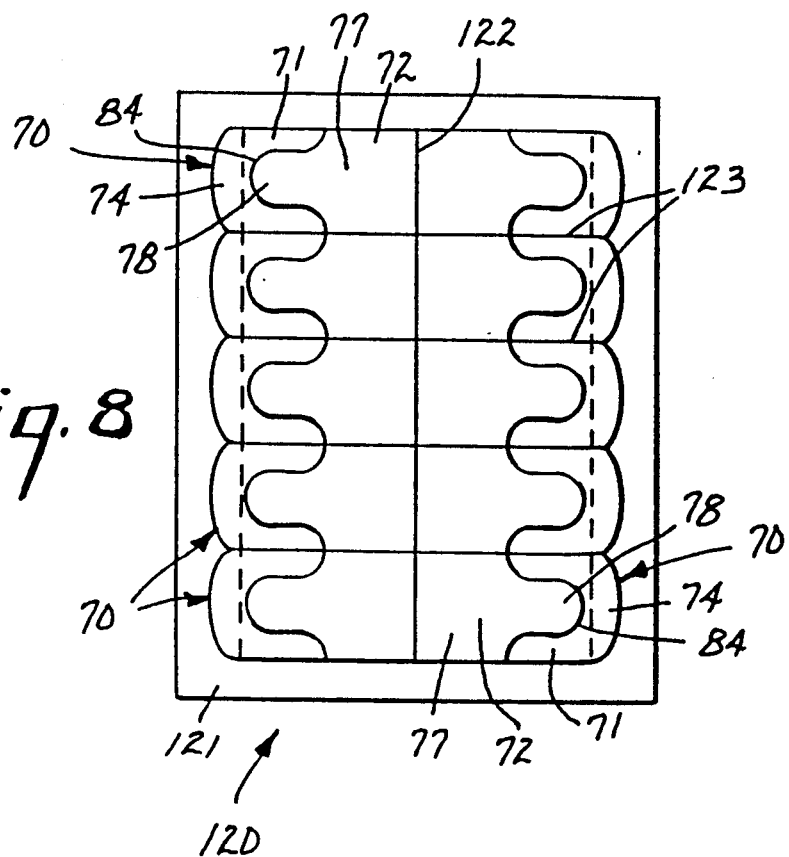
FIG. 8 is a top plan view of a second embodiment of an assembly of biomedical electrodes.

FIG. 8 illustrates a strip 120 of electrodes, which can be either electrode 40 or electrode 70. In FIG. 8, the strip 120 of electrode 70 are assembled onto a release liner 121 during manufacture. The plurality of electrodes 70 comprising strip 120 can be packaged in a flat condition to minimize storage space. The number of electrodes 70 comprising strip 120 can be adjusted to match the number of electrodes 70 to be used in a particular diagnostic or other medical procedure.

Each electrode 70 has a separator construction 71 and a conductor member 72 over a field 73 of adhesive(s), except for lift tab portion 74 which extends beyond field 73.

Each of the electrodes 70 are contiguous to another electrode 70 along lines 122 and 123. Line 122 separates contiguous electrodes 70 at their pad portions 77. Lines 123 separate contiguous electrodes 70 between adjacent tab portions 78.

Figure 9:
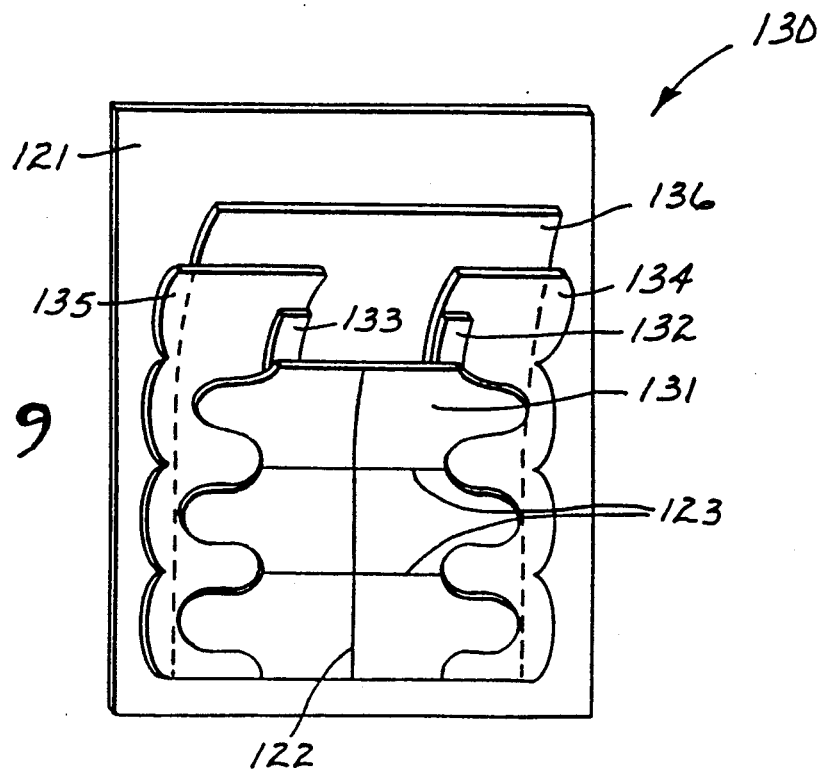
FIG. 9 is an illustrative view of first steps of a means of assembly of a biomedical electrode array useful for providing the assembly of biomedical electrodes shown in FIG. 8.

FIG. 9 shows the construction of an electrode array subassembly 130 on release liner 121. Subassembly 130 has a laminate construction comprising a strip 131 of a series of unseparated, mirrored conductor members, two strips 132 and 133 of double-stick adhesive, two strips 134 and 135 of separator construction, and a field 136 of adhesive(s). Each strip 131, 132, 133, 134, 135, and 136 is sequentially aligned as shown in FIG. 9 according to processes and with equipment known to those skilled in the art for the assembly of laminate constructions including adhesive layers. U.S. Pat. No. 4,795,516 (Strand) and U.S. Pat. No. 4,798,642 (Craighead) disclose processes and equipment useful for preparing a strip subassembly 130 on release liner 121. The width of the electrode strip subassembly 130 is about 4-16 cm and preferably about 8 cm.

This strip subassembly 130 is sequentially constructed preferably by overlaying strips 132 and 133, preferably concurrently, on the surface of strip 131 which is electrically conductive in a position where pad portion 77 becomes tab portion 78, as seen in FIG. 4. Next, strip 134 is applied to adhesive strip 132 such that separator construction strip 134 covers adhesive strip 132 at an area adjacent to edge 82 as seen in FIG. 4. Likewise, and preferably concurrently with the overlay of strip 134 on strip 132, separator construction strip 135 is laid over adhesive strip 133 in a symmetrical manner on subassembly 130. Next, depending on whether conductive adhesive is intended to comprise field 73 or field 73a, biocompatible adhesive (either conductive adhesive or skin adhesive) is laid over separator construction strips 134 and 135 and conductive adhesive is laid over the area between separator construction strips 134 and 135 to contact conductor member strip 131. Preferably, a single field 136 of conductive adhesive is laid over strip subassembly 130 thus far constructed, preferably extending from separator construction strip 134 to separator construction strip 135, except that field 136 does not overlay construction strips 134 and 135 in those areas distal from conductor member strip 131, in order to create opposing lift tab portions on subassembly 130. Next, the release liner 121 is laid over field 136 of adhesive.

Strip subassembly 130 is then separated into individual electrodes 70 as seen in FIG. 8 by cutting along line 122 to bisect subassembly 130 into two rows of electrode strips and then cutting along lines 123 to separate each electrode 70 on release liner 121, thereby producing a plurality of electrodes 70 seen in FIG. 8.

While it is understood that the methods of construction described with respect to FIG. 7 and the method of construction described with respect to FIG. 9 both apply sequential alignment of multiple layers to form a laminate, the order in which the multiple layers are overlaid may be reversed or otherwise configured. Thus, the method of construction with respect to FIG. 7 can begin first with conductor members 118 and conclude with conductive adhesive 112, whereas the method of construction with respect to FIG. 9 can begin with release liner 121 and conclude with overlaying of conductor member strip 131.

It is noted that for all embodiments shown and described, the conductor member 42 and 72 was depicted in substantially the same manner, i.e., as having a rather large, rectangular, pad portion with an elongate narrow tab portion. It will be understood that a variety of shapes may be utilized; however, the shape described is particularly efficient in that it provides for a good tab portion readily engagable by a clip, such as clip 7, FIG. 1, and it provides for a pad portion having a relatively large surface area While a variety of materials may be utilized for the conductor member, such as conductor members 16, 42, and 72, preferably the relatively flat, thin and flexible construction results from a material, such as a plastic material, having a conductive material capable of recovering electrical performance after cardiac de-fibrillation procedures such as a silver/silver chloride conductive coating on at least one side thereof, or an electrically conductive carbon-containing web on at least one side thereof. If only one side of the conductor member has a conductive layer thereon, it will generally be that side which corresponds to the side of the pad portion projecting toward conductive adhesive, and the portion of the tab portion facing the separator construction.

It is foreseen that a typical conductor member 42 and 72 will comprise a strip of material having a thickness of about 0.05-0.2 millimeters, such as polyester film having a coating of silver/silver chloride of about 2.5-12 micrometers, and preferably about 5 micrometers thick thereon. Presently preferred is a polyester film commercially available as "Mellinex" 505-300, 329, or 339 film from ICI Americas of Hopewell, Va. coated with a silver/silver chloride ink commercially available as "R-300" ink from Ercon, Inc. of Waltham, Mass. For conductor member 42 or 72 made of a nonwoven web, a web of polyester/cellulose fibers commercially available as "Manniweb" web from Lydall, Inc. of Troy, N.Y. having a carbon ink commercially available as "SS24636" ink from Acheson Colloids Company of Port Huron, Mich. can be used. To enhance mechanical contact between clip 7 and conductor member 42 or 72, an adhesively-backed polyethylene tape can be applied to the conductor member tab portion on the side opposite the side having the conductive coating A surgical tape commercially available from 3M Company as "Blenderm" tape can be employed for this purpose.

It will be understood that such arrangements are not only flat, thin and flexible, but they will not be likely to render substantial shadows in X-rays. Thus, a patient wearing preferred biomedical electrodes according to the present invention can be subjected to X-ray tests without the need for removal (and accompanying discomfort and inconvenience) and reattachment of the biomedical electrode disclosed herein.

While a variety of shapes and sizes of conductor members may be used, preferred applications involve conductor members with pad portions about 1-3 cm by 1-2 cm and tab portions or tongues about 1-3 cm long by 0.5-1.5 cm wide.

It will also be understood that a variety of materials may be utilized as a biocompatible skin adhesive as field portion 43b or 73b. Typically, acrylate ester adhesives will be preferred. Acrylate ester copolymer adhesives are particularly preferred. Such adhesives are generally described in U.S. Pat. Nos. 2,973,826; Re 24,906; Re 33,353; 3,389,827; 4,112,213; 4,310,509; 4,323,557; 4,732,808; 4,917,928; 4,917,929 and European Patent Publication 0 051 935, all incorporated herein by reference.

In particular, an adhesive copolymer having from about 95 to about 97 weight percent iso-octyl acrylate and from about 5 to about 3 weight percent acrylamide and having an inherent viscosity of 1.1-1.25 dl/g is presently preferred.

Adhesive useful as means for adhering 44 or 79 can be any of the acrylate ester adhesives described for the biocompatible skin adhesive. A presently preferred adhesive is the same adhesive as presently preferred for the biocompatible skin adhesive except having an inherent viscosity of about 1.3-1.45 dl/g.

For the conductive adhesive, conductive adhesives such as those described in U.S. Pat. No. 4,848,353 (incorporated herein by reference) will be preferred. In particular, an adhesive having the following ingredients is foreseen as a useful material:

|  | Dry Weight Percent |
| --- | --- |
| Copolymer: | |
| Acrylic Acid | 9.50 |
| N-vinyl pyrrolidone | 9.50 |
| Glycerin | 51.58 |
| Guar Gum | 0.12 |
| Water | 25.50 |
| Sodium hydroxide | 2.64 |
| Benzildimethylketal | 0.07 |
| Potassium chloride | 1.00 |
| TEGBM (triethylene glycol bis (methacrylate)) | 0.09 |

| -continued | |
| --- | --- |
| | Dry Weight Percent |
| | 100.00 |

It is also preferred to cure the adhesive precursor on a thin support web, e.g., 0.1 mm Cerex ™ material (available from Monsanto Co., St. Louis, Mo.), to facilitate mechanical handling in manufacturing processes.

Separator construction 41 or 71 can be made of a non-conductive natural or synthetic material, conveniently transparent or translucent material enabling one to see the condition of conductive adhesive 43 and its contact with skin of a patient wearing electrode 40 or 70. Presently preferred separator construction 41 or 71 is polyethylene terephthalate and between about 0.05 and 0.08 mm thick. A commercially available polyethylene terephthalate film is "Mellinex" polyester film from ICI Americas, Hopewell, Va. having a thickness of 0.05 mm. Alternatively, an adhesively backed polyethylene tape can be used for separator construction 41 or 71. A surgical tape commercially available from 3M Company as "Blenderm" tape can be employed. The tape can be folded near pad portion 51 or 77 to create means for adhering 44 or 79. But the adhesive must be covered with spacer to detackify lift tab portion 74.

Again, it will be understood that the previously recited examples are exemplary only of the invention, and the invention is not to be limited by the specific materials, dimensions, forms or arrangements described and/or shown in the drawings.

What is claimed is:

1. A method of making biomedical electrode, comprising:
   (a) providing a strip of conductive members, each member having two tab portions at opposing edges of the strip and two pad portions integral and continuous on the strip;
   (b) overlaying a means for adhering on the strip of conductor members on each tab portion in a position substantially adjacent to each pad portion;
   (c) overlaying a separator construction on each means for adhering and over each tab portion on each conductor member;
   (d) overlaying a field of conductive adhesive over each pad portion of each conductive member and optionally over each separator construction to form an electrode array;
   (e) overlaying a release liner on the electrode array;
   (f) cutting the electrode array on the release liner along a line between adjacent tab portions; and
   (g) cutting the electrode array along a line between continuous pad portions, whereby a plurality of individual biomedical electrodes, each having a centrally-positioned tab portion, are provided on the release liner.

2. The method according to claim 1, wherein an edge of said separator construction extends beyond an edge of said conductive adhesive.

3. The method according to claim 1, further comprising between steps (d) and (e) the step of overlaying a field of biocompatible skin adhesive over each separator construction.

* * * * *